(12) United States Patent
Zarnegar et al.

(10) Patent No.: US 12,708,591 B2
(45) Date of Patent: Aug. 18, 2026

(54) SELF COLLAPSING FEEDING TUBE WITH CLEANING MECHANISM

(71) Applicant: Cornell University, Ithaca, NY (US)

(72) Inventors: Rasa Zarnegar, New York, NY (US); Thomas Ciecierega, Wyckoff, NJ (US); Carl Crawford, New York, NY (US); Brendan Finnerty, New York, NY (US); Thomas Fahey, III, Larchmont, NY (US)

(73) Assignee: Cornell University, Ithaca, NY (US)

( * ) Notice: Subject to any disclaimer, the term of this patent is extended or adjusted under 35 U.S.C. 154(b) by 1024 days.

(21) Appl. No.: 16/969,757

(22) PCT Filed: Feb. 14, 2019

(86) PCT No.: PCT/US2019/017990

§ 371 (c)(1),
(2) Date: Aug. 13, 2020

(87) PCT Pub. No.: WO2019/161042

PCT Pub. Date: Aug. 22, 2019

(65) Prior Publication Data

US 2020/0397667 A1 Dec. 24, 2020

Related U.S. Application Data

(60) Provisional application No. 62/630,525, filed on Feb. 14, 2018.

(51) Int. Cl.
*A61J 15/00* (2006.01)
*A61M 39/08* (2006.01)

(52) U.S. Cl.
CPC ....... *A61J 15/0038* (2013.01); *A61J 15/0026* (2013.01); *A61M 39/08* (2013.01); *A61M 2209/10* (2013.01)

(58) Field of Classification Search
CPC ................ A61J 15/0038; A61J 15/0026; A61J 15/0015; A61M 2209/10; A61M 2025/0233
See application file for complete search history.

(56) References Cited

U.S. PATENT DOCUMENTS 3,717,151 A * 2/1973 Collett .............. A61M 25/0606 604/106
3,815,608 A * 6/1974 Spinosa ................ A61M 25/04 604/105

(Continued)

OTHER PUBLICATIONS

International Search Report and Written Opinion in International Patent Application No. PCT/US2019/017990 dated May 1, 2019.

(Continued)

*Primary Examiner* — Bhisma Mehta
*Assistant Examiner* — Adam J. Cermak
(74) *Attorney, Agent, or Firm* — Foley & Lardner LLP

(57) ABSTRACT

A delivery device, such as a feeding tube, may have one or more pullout resistors that can anchor the delivery device to a patient's abdomen. When implanted, the pullout resistors can lie between the small intestine and intraabdominal wall. The pullout resistors can prevent inadvertent retrograde displacement of the delivery device without obstructing the lumen of the intestine. The pullout resistors can be flexible to enable a healthcare professional to apply an external retraction force to remove the delivery device.

19 Claims, 10 Drawing Sheets

(56) References Cited

U.S. PATENT DOCUMENTS 4,311,148 A * 1/1982 Courtney .............. A61M 25/02 604/362
4,668,225 A * 5/1987 Russo ................ A61J 15/0038 604/93.01
5,073,166 A * 12/1991 Parks ................. A61J 15/0015 604/105
5,080,650 A 1/1992 Hirsch et al.
5,092,850 A * 3/1992 Buma .............. A61M 39/0247 604/910
5,356,391 A * 10/1994 Stewart .............. A61J 15/0038 604/174
5,460,603 A * 10/1995 DeSantis ............ A61J 15/0015 604/323
6,039,714 A * 3/2000 Cracauer ............ A61J 15/0038 604/174
6,186,985 B1 * 2/2001 Snow ................. A61J 15/0015 604/264
6,322,538 B1 * 11/2001 Elbert ................ A61J 15/0038 604/105
6,464,686 B1 * 10/2002 O'Hara ............... A61J 15/0019 604/539
6,729,334 B1 * 5/2004 Baran .............. A61M 16/0463 128/207.14
8,622,968 B2 * 1/2014 Watanabe ........... A61J 15/0038 604/174
9,107,810 B2 * 8/2015 Bailey ................. A61J 15/0038
10,695,270 B2 * 6/2020 Benuri-Silbiger .. A61J 15/0038
2003/0109830 A1 * 6/2003 Picha .................. A61J 15/0061 604/174
2004/0181194 A1 * 9/2004 Perkins ................ B08B 9/0436 134/8
2005/0288722 A1 * 12/2005 Eigler .................. A61N 1/3629 607/9
2009/0143713 A1 * 6/2009 Van Dam ........... A61M 27/008 604/9
2011/0009828 A1 * 1/2011 Prechtel ............. A61J 15/0065 604/175
2011/0313359 A1 * 12/2011 Cohen ................. A61J 15/0057 604/175
2014/0207071 A1 * 7/2014 Williams ............ A61J 15/0065 604/177
2017/0367932 A1 * 12/2017 Millis ................. A61J 15/0015
2019/0021762 A1 * 1/2019 Millis ................. A61J 15/0015

OTHER PUBLICATIONS

International Preliminary Report on Patentability in International Application PCT/US2019/017990 dated Aug. 27, 2020.

* cited by examiner 104
112
600
602
500
308

104
600
112
300
504
500
600
502
600

SELF COLLAPSING FEEDING TUBE WITH CLEANING MECHANISM

CROSS REFERENCE TO RELATED APPLICATION

This application is a U.S. National Stage Application under 35 U.S.C. § 371 of International Application No. PCT/US2019/017990, filed on Feb. 14, 2019, which claims priority to and the benefit of U.S. Provisional Application No. 62/630,525, filed on Feb. 14, 2018, which are herein incorporated by reference in their entireties.

BACKGROUND OF THE DISCLOSURE

Jejunostomy feeding tubes (J-tube) are often needed to support the enteral nutritional needs of a patient during both short and long-term illnesses. The catheters used today can be simple red-rubber tubes about 30 centimeters in length that are placed surgically through the abdominal wall and inserted into the proximal small intestine. The feeding tube can be anchored to the skin with a simple suture into the skin that is wrapped around the tube externally.

SUMMARY OF THE DISCLOSURE

The present disclosure describes a delivery device. The delivery device can be a feeding tube. For example, the delivery device can be a transabdominal feeding jejunostomy tube. The delivery device can be implanted in patients that require external nutrition via the small intestine or stomach for any specified length of time.

The delivery device of the present disclosure can include one or more pullout resistors that can anchor the delivery device to the patient's abdomen. The pullout resistors can reduce feeding tube migration. The delivery device can include pullout resistors that anchor the delivery device with the abdomen rather than inflatable bumpers or balloons because, when inflated, the bumper or balloon can expand within the lumen of the intestine and can obstruct the flow of proximal intestinal contents due to the large size of the inflated bumper or balloon.

To reduce migration, the delivery device can include flexible intraperitoneal pullout resistors that can lie between the small intestine and intra-abdominal wall. The pullout resistors 104 can prevent inadvertent retrograde displacement of the delivery device without obstructing the lumen of the intestine. The pullout resistors can be flexible to enable a healthcare professional to apply an external retraction force to remove the delivery device.

According to at least one aspect of the disclosure, a delivery device can include an elongated structure that can include a first opening at a first end of the tube and a second opening at a second end of the elongated structure. The elongated structure can define a lumen between the first opening and the second opening for delivery of a fluid to a subject in which the elongated structure is inserted. The delivery device can include a pullout resistor extending from an external surface of the elongated structure between the first end of the tube and the second end of the elongated structure. The pullout resistor can anchor the elongated structure with an interior portion of an abdominal wall of the subject when the pullout resistor is in a first state and collapse from the first state to a second state when a predetermined amount of force is applied in a direction along a longitudinal axis of the elongated structure.

The delivery device can include a washer configured to slide along a length of the longitudinal axis of the elongated structure to clamp the abdominal wall of the subject between the washer and the pullout resistor. The pullout resistor can include a plurality of retaining members projecting perpendicular to the external surface of the elongated structure.

The plurality of retaining members can project perpendicular to the external surface of the elongated structure in the first state and deflect toward the external surface of the elongated structure in the second state. Each of the plurality of retaining members has a thickness between 0.5 mm and 5 mm. Each of the plurality of retaining members has a length between 3 mm and 15 mm. The predetermined amount of force is between 5 lbs and 10 lbs.

In some implementations, the delivery device can include a radiopaque strip extending along at least a portion of the elongated structure. The elongated structure can include at least one of silicone, latex, polytetrafluoroethylene, polyethylene, polyurethane, or polyvinyl chloride. The elongated structure comprises an antibiotic or antimicrobial coating.

According to at least one aspect of the disclosure, a kit can include a delivery device. The delivery device can include an elongated structure that can include a first opening at a first end of the elongated structure and a second opening at a second end of the elongated structure. The elongated structure can define a lumen between the first opening and the second opening for delivery of a fluid to a subject in which the elongated structure is inserted. The delivery device can include a pullout resistor extending from an external surface of the elongated structure between the first end of the elongated structure and the second end of the elongated structure. The pullout resistor can anchor the elongated structure with an interior portion of an abdominal wall of the subject when the pullout resistor is in a first state and collapse from the first state to a second state when a predetermined amount of force is applied in a direction along a longitudinal axis of the elongated structure. The kit can include a washer configured to slide along a length of the elongated structure to couple the abdominal wall between the washer and the pullout resistor. The kit can include a brush configured to slide within the lumen of the elongated structure.

In some implementations, the brush has a length less than a length of the delivery device. The pullout resistor can include a plurality of retaining members projecting perpendicular to the external surface of the elongated structure. The plurality of retaining members can project perpendicular to the external surface of the elongated structure in the first state and deflect toward the external surface of the elongated structure in the second state.

According to at least one aspect of the disclosure, a method to surgically place a delivery device with an abdomen of a subject can include providing a delivery device. The delivery device can include an elongated structure that can include a first opening at a first end of the elongated structure and a second opening at a second end of the elongated structure. The elongated structure can define a lumen between the first opening and the second opening for delivery of a fluid to a subject in which the elongated structure is inserted. The delivery device can include a pullout resistor extending from an external surface of the elongated structure between the first end of the elongated structure and the second end of the elongated structure. The pullout resistor can anchor the elongated structure with an interior portion of an abdominal wall of the subject when the pullout resistor is in a first state and collapse from the first state to a second state when a predetermined amount of force is applied in a direction along a longitudinal axis of the elongated structure. The method can include passing the elongated structure of the delivery device through an incision in the abdominal wall of the subject.

In some implementations, the method can include coupling a washer to a position along the longitudinal axis of the elongated structure to clamp the abdominal wall of the subject between the washer and the pullout resistor. The pullout resistor can include a plurality of retaining members projecting perpendicular to the external surface of the elongated structure. Each of the plurality of retaining members has a thickness between 0.5 mm and 5 mm and a length between 3 mm and 15 mm. The method can include deploying the pullout resistor from the second state to the first state.

In some implementations, the method can include applying the predetermine force in the direction along the longitudinal axis of the elongated structure to collapse the pullout resistor from the first state to the second state and removing the elongated structure from the incision in the abdominal wall of the subject.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a delivery device. The delivery device of the present disclosure can include one or more pullout resistors that can anchor the delivery device to the patient's abdomen. The pullout resistors can reduce feeding tube migration. The delivery device can include pullout resistors that anchor the delivery device with the abdomen rather than inflatable bumpers or balloons that can obstruct the intestine. When implanted, the pullout resistors can lie between the small intestine and intra-abdominal wall. The pullout resistors can prevent inadvertent retrograde displacement of the delivery device without obstructing the lumen of the intestine. The pullout resistors can be flexible to enable a healthcare professional to apply an external retraction force to remove the delivery device.

Figure 1:
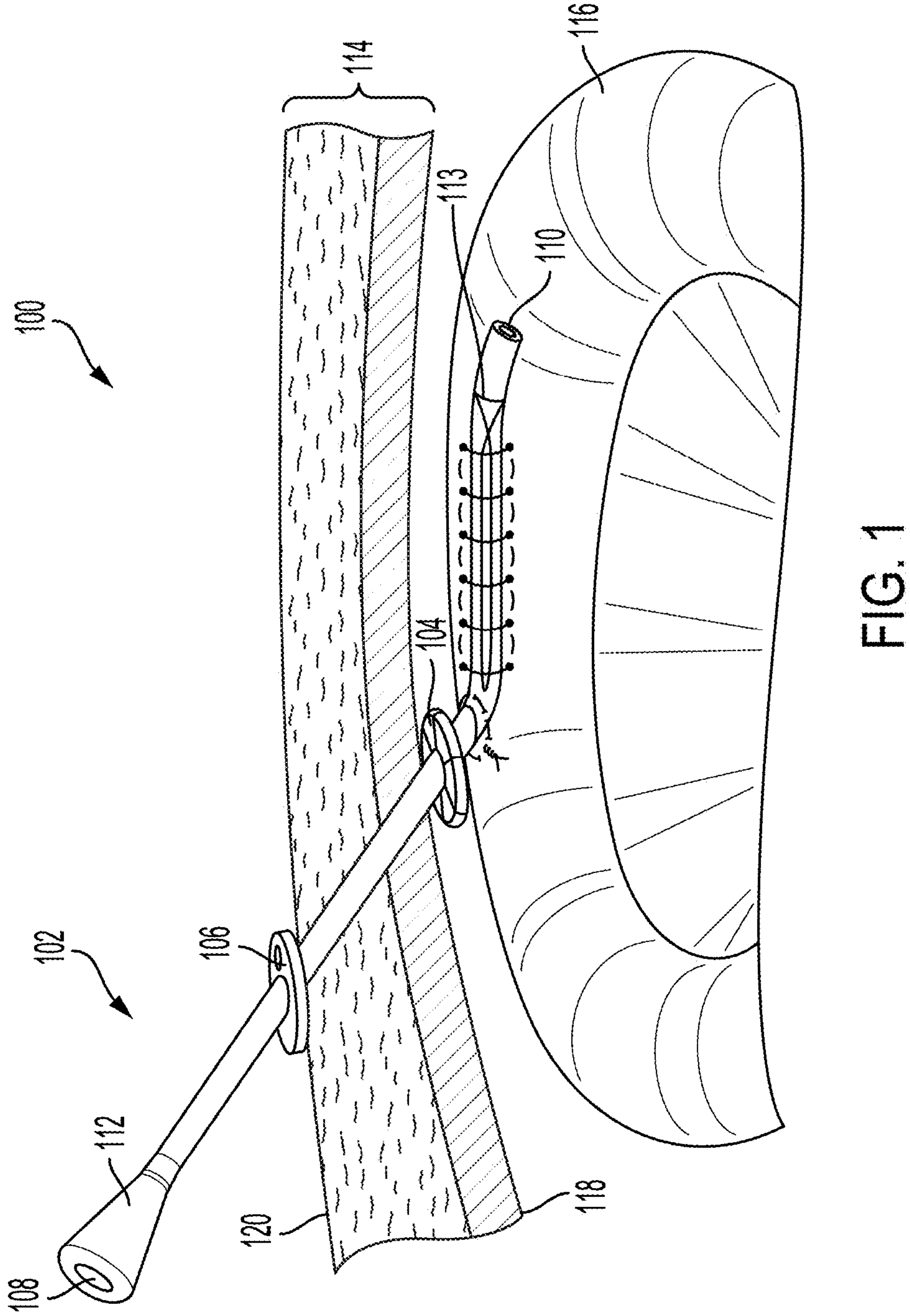
FIG. 1 illustrates an example environment with an example delivery device implanted into the small intestine of a patient.

FIG. 1 illustrates an example environment 100 with an example delivery device 102 implanted into the small intestine 116 of a patient. The delivery device 102 can include a pullout resistor 104 that can anchor the delivery device 102 to an intraperitoneal face 118 of the abdominal wall 114, for example. The delivery device 102 can also be anchored to the patient by a washer 106 that can anchor the delivery device 102 with a second surface 120. The second surface 120 can be the skin of the patient. The delivery device 102 can include elongated structure 112 that can define a lumen. The elongated structure 112 can include a first opening 108 at a first end and a second opening 110 at a second end. The opening 110 can be implanted into the small intestine 116 of the patient. The first end, exterior to the patient, can be referred to as an anterior end. The second end, interior to the patient, can be referred to as a distal end.

The delivery device 102 can be a feeding tube with collapsing pullout resistors 104 and washers 106. The elongated structure 112 of the delivery device 102 is described further in relation to FIG. 2, among others. The pullout resistor 104 and the washer 106 are described further in relation to FIGS. 3-9, among others. As an overview, the delivery device 102 can pass through the abdominal wall 114 and into the small intestine 116 (or other target location such as the stomach) of the patient. The delivery device 102 can include a pullout resistor 104, which can be an internal anchor for the delivery device 102. The delivery device 102 can include washer 106, which can be an external anchor for the delivery device 102. The pullout resistor 104 and the washer 106 can secure the delivery device 102 with the abdominal wall 114 to prevent the accidental removal of the delivery device 102 from the patient's small intestine 116. The opening 108 and the opening 110 can be opposite openings of a lumen defined within the elongated structure 112. The lumen can enable passage of fluids from the opening 108 to the opening 110 to provide nutrients to the, as illustrated in FIG. 1, small intestine 116 of the patient.

Figure 2:
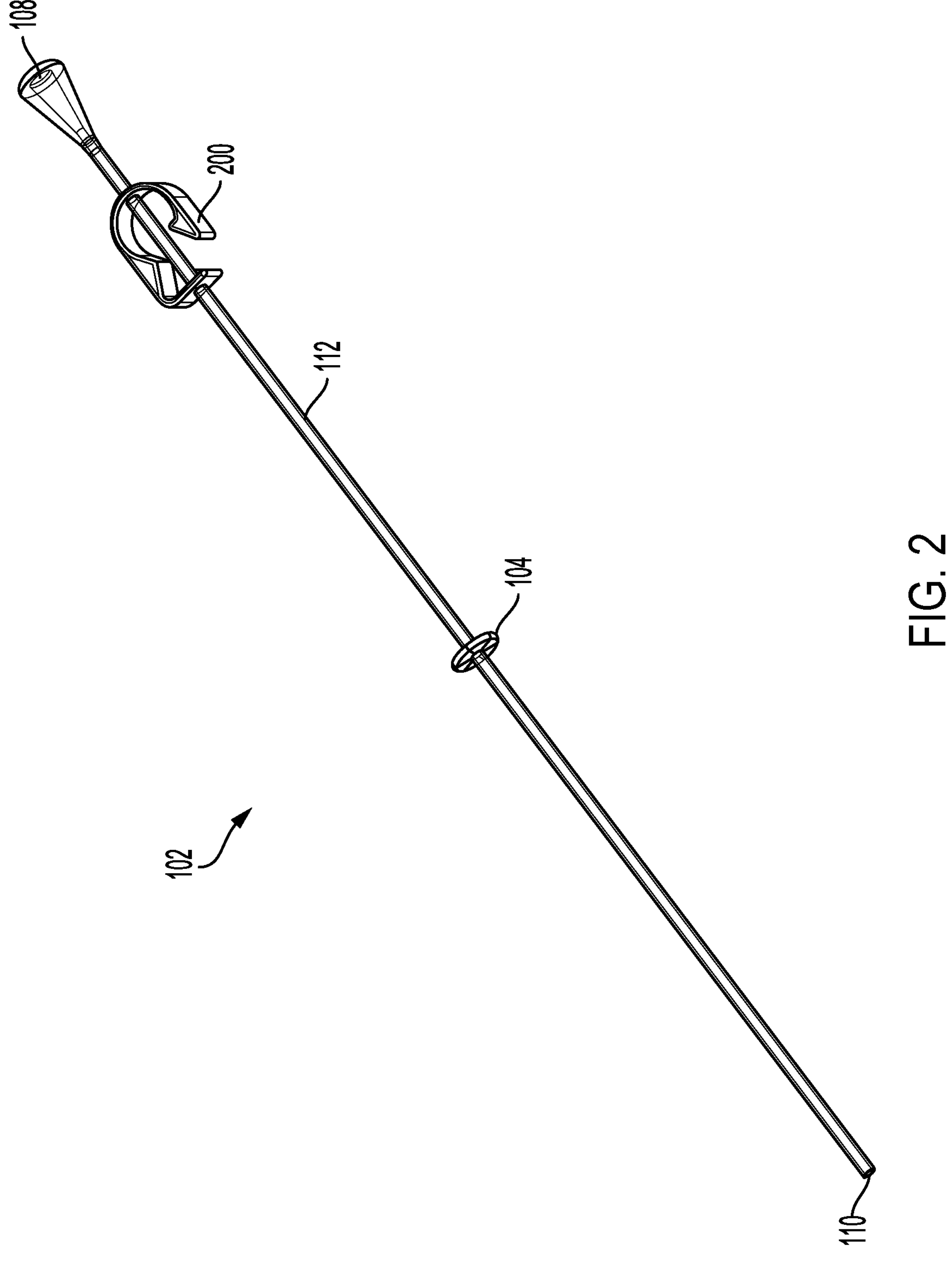
FIG. 2 illustrates an example delivery device that can be used in the environment illustrated in FIG. 1.

FIG. 2 illustrates an example delivery device 102. The delivery device 102 can include an elongated structure 112. The elongated structure 112 can be a tube. The elongated structure 112 can have a length between about 15 cm and about 50 cm, between about 20 can be and about 50 cm, or between about 20 cm and about 40 cm. In some implementations, the length of the elongated structure 112 can be longer than needed for an implantation surgery and a surgeon can cut the elongated structure 112 to length during or before the implantation surgery. For example, initially the elongated structure 112 can be 60 cm and prior to implantation into a pediatric patient, the surgeon can remove a portion of the anterior or distal end of the elongated structure 112. The elongated structure 112 can be cut with surgical scissors or other cutting device. The elongated structure 112 can have an internal diameter of about 5 French, about 6 French, about 7 French, about 8 French, about 9 French, about 10 French, about 11 French, about 12 French, or about 13 French. The elongated structure 112 can have an outer diameter of about 5 French, about 6 French, about 7 French, about 8 French, about 9 French, about 10 French, about 11 French, about 12 French, about 13 French, about 14 French, about 15 French, about 16 French, about 17 French, or about 18 French.

The elongated structure 112 can include a biocompatible material. In some implementations, the elongated structure 112 can include silicone, latex, polytetrafluoroethylene, polyethylene, polyurethane, polyvinyl chloride, or other polymer. In some implementations, elongated structure 112 can be impregnated or covered with an antibiotic or antimicrobial material. For example, the elongated structure 112 can include silver. The elongated structure 112 can be visually opaque. The elongated structure 112 can be substantially clear to enable a patient or healthcare professional to view the contents (or blockages) within the internal lumen of the elongated structure 112. The elongated structure 112 can include a radiopaque strip 113 extending along a length of the elongated structure 112. For example, the elongated structure 112 can include a metal or barium sulfate strip embedded within the elongated structure 112 that is detectable by a medical imaging system, such as an x-ray or computed tomography imaging. In some implementations, only a distal portion of the elongated structure 112 includes a radiopaque material to enable a healthcare professional to view the position of the distal end of the elongated structure 112 within the patient.

The delivery device 102 can include one or more pullout resistors 104. The pullout resistor 104 is described further in relation to FIGS. 3-9, among others. The pullout resistor 104 can anchor the delivery device 102 to the patient. The pullout resistor 104 can anchor the delivery device 102 to the patient's abdominal wall 114. The pullout resistor 104 and the washer 106 can anchor the delivery device 102 to the patient's abdominal wall. For example, the pullout resistor 104 can be deployed at the intraperitoneal face 118 of the patient's abdominal wall 114. The washer 106 can be deployed at the surface 120 of the abdominal wall 114. In some implementations, the surface 120 can be the skin surface of the patient's abdomen. During implantation, a healthcare professional can push the washer 106 distally along the longitudinal axis of the elongated structure 112 toward the surface 120. When the washer 106 is in contact with the surface 120, movement of the washer 106 along the longitudinal axis and toward the distal end of the elongated structure 112 draws the pullout resistor 104 toward the intraperitoneal face 118 of the abdominal wall 114—clamping the abdominal wall 114 between the pullout resistor 104 and the washer 106. The healthcare professional can stop pushing the washer 106 distally along the longitudinal axis of the elongated structure 112 when the pullout resistor 104 comes into contact with the intraperitoneal face 118. When the washer 106 is in its deployed position along the longitudinal axis of the elongated structure 112, the abdominal wall 114 can be clamped between the pullout resistor 104 and the washer 106. The washer 106 can be secured in place with a clamp, suture, lock ring, or other barrier. In some implementations, anchoring the delivery device 102 to the patient with the pullout resistor 104 and washer 106 does not include physically securing the delivery device 102 to the patient. For example, the delivery device 102 is not secured with sutures, glue, or tape to a surface of the patient. The clamping force of the washer 106 pushing inward and the pullout resistor 104 pushing outward can be less than rotational forces of friction of the pullout resistor 104 and the washer 106 on the abdominal wall 114 such that the delivery device 102 can rotated within the incision to prevent encapsulation of delivery device 102 as the incision site heals. For example, postoperatively, a patient may rotate the delivery device 102 half a turn to prevent the wound site from binding with the delivery device 102.

In some implementations, rather than the washer 106 and the pullout resistor 104 both simultaneously applying a clamping force to the abdominal wall 114, the pullout resistor 104 and the washer 106 can serve as stops for the travel of the delivery device 102 along its longitudinal axis. For example, the washer 106 can be coupled to a first axial location of the delivery device 102 to prevent the delivery device 102 from being pushed distally (or further) into the patient. The pullout resistor 104 can be coupled to a second axial location of the delivery device 102 to prevent the delivery device 102 from being pulled arterially (or out of) the patient. The distance between the first position and the second position can be greater than the thickness of the abdominal wall 114 such that only one of the pullout resistor 104 or the washer 106 comes into contact with the abdominal wall 114 at any given time. In some implementations, the delivery device 102 can be used with only a pullout resistor 104 to prevent the delivery device 102 from being accidentally removed from the patient.

To remove the delivery device 102 from the patient, a healthcare professional can apply a predetermined force along the longitudinal axis of the elongated structure 112. For example, the healthcare professional can grasp the distal end of the elongated structure 112 near the opening 108 and pull the delivery device 102 away from the patient. The force of the abdominal wall 114 against the pullout resistor 104 can cause the pullout resistor 104 to collapse or deflect from a first state (e.g., a deployed state) to a second state (e.g., a collapsed or retracted state). When deployed, the pullout resistor 104 is substantially perpendicular to the longitudinal axis of the elongated structure 112. In the collapsed state, the pullout resistor 104 collapses inward toward the external surface of the elongated structure 112. In some implementations, the force to collapse the pullout resistor 104 from the first state to the second state can be at least 3 lbs, at least 4 lbs, at least 5 lbs, at least 6 lbs, at least 7 lbs, at least 8 lbs, at least 9 lbs, at least 10 lbs, at least 11 lbs, at least 12 lbs, at least 13 lbs, at least 14 lbs, or at least 15 lbs. The force can be between about 3 lbs and about 20 lbs, between about 5 lbs and about 15 lbs, or between about 5 lbs and about 10 lbs.

The washers 106 can be pullout resistors 104. The washers 106 can be pullout resistors 104 that are removable from the elongated structure 112. For example, the pullout resistor 104 can be integral to the elongated structure 112 while the washer 106 is removable and a surgeon can couple the washer 106 with the elongated structure 112 once the pullout resistor 104 is within the intraperitoneal space of the subject. In some implementations, the washer 106 can be coupled with the elongated structure 112 and be configured to slide along the longitudinal axis of the elongated structure 112. For example, a surgeon can slide the washer 106 toward the pullout resistor 104 to clamp the abdominal wall 114 between the (stationary) pullout resistor 104 and the washer 106. The washer 106 can be secured to a position along the longitudinal axis of the elongated structure 112 with friction. For example, a clamp or press fitting can hold the washer 106 at a longitudinal position. In some implementations, the washer 106 can be secured to at a longitudinal position with glue or a suture. As described below, the pullout resistor 104 can include retaining members. In some implementations, the pullout resistor 104 does not include retaining members.

The delivery device 102 can include a closure device 200. The closure device 200 can be a medical tubing clamp (e.g., an IV or catheter clamp). The closure device 200 can be a single-position clamp that when in the closed, locked position applies pressure to the elongated structure 112 to collapse the elongated structure 112 and prevents retrograde fluid flow. For example, when a patient or healthcare professional is not flowing a fluid through the delivery device 102 and into the patient, the closure device 200 can be closed to prevent fluid from flowing out of the patient's small intestine 116 (or stomach) and out through the elongated structure 112. The closure device 200 can be a multi-position clamp that enables a patient or healthcare professional to partially occlude or close the elongated structure 112 to control the rate at which fluid can enter the patient via the delivery device 102. In some implementations, the closure device 200 can include a valve. For example, the closure device 200 can be or can include a stopcock. The closure device 200 can be a 1-way, 2-way, 3-way, or 4-way stopcock. In some implementations, tubing can be coupled with the delivery device 102 at the stopcock. For example, a Foley or other catheter bag can be coupled with the stopcock to enable the patient or healthcare professional to release gas from the patient's stomach. Liquid that may be released with the gas exiting the patient can be captured in the catheter bag.

Figures 3, 4:
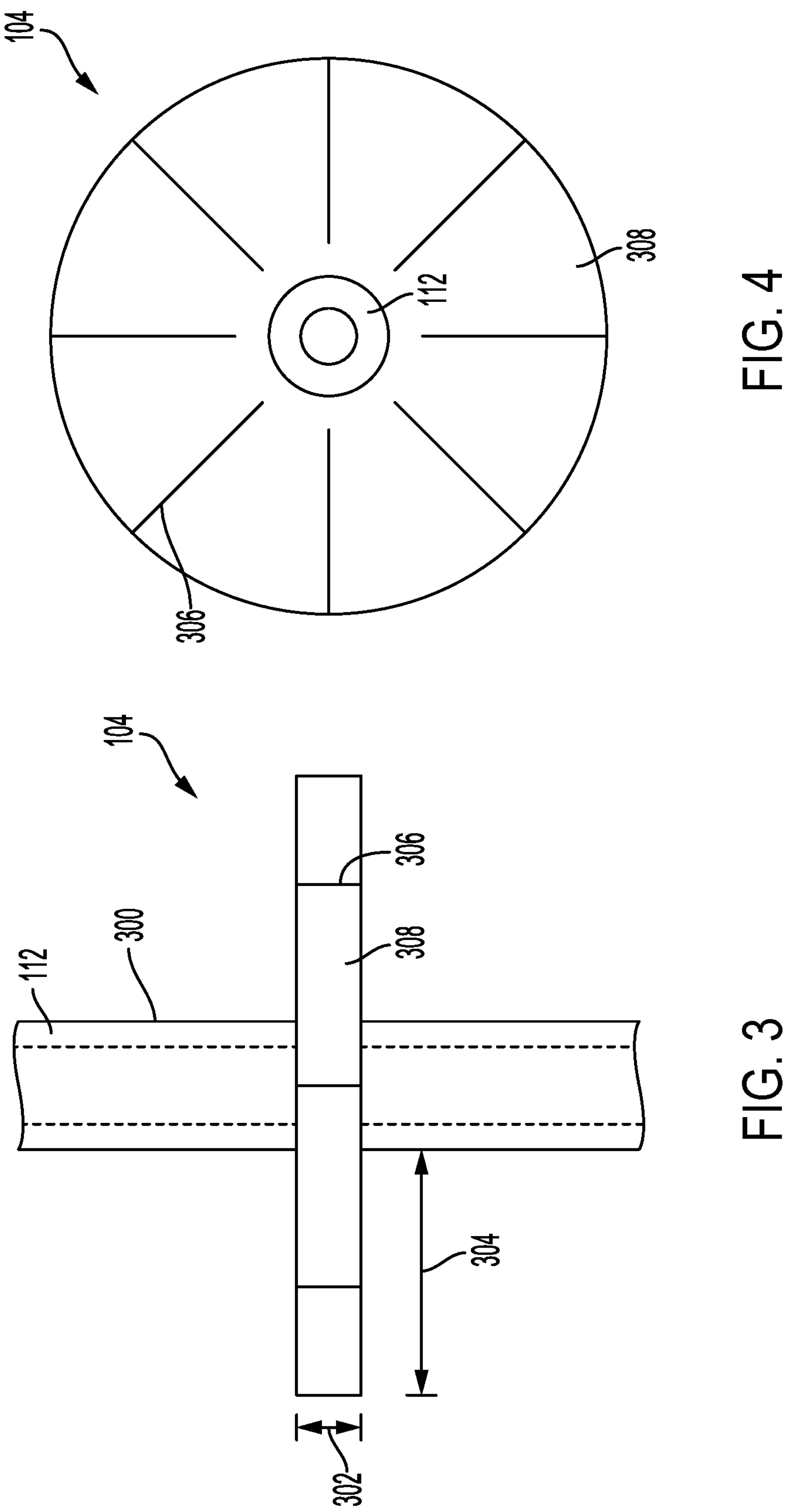
FIGS. 3 and 4 illustrate front and top views of an example pullout resistor that can be used with the example delivery device illustrated in FIG. 2.

FIGS. 3 and 4 illustrate front and top views, respectively, of an example pullout resistor 104. Referring to FIGS. 3 and 4 together, the pullout resistor 104 can include a plurality of retaining members 308 that extend from the elongated structure 112 when in the deployed state. In the deployed state, the retaining members 308 can be substantially perpendicular to the longitudinal axis of the elongated structure 112. In some implementations, the retaining members 308 can form an angle between about 300 and about 90°, between about 450 and about 90°, between about 550 and about 90°, between about 65 and about 90°, between about 750 and about 90°, or between about 850 and about 90° with the longitudinal axis of the elongated structure 112 when in the deployed state. In the collapsed state, the retaining members 308 can form an angle with the longitudinal axis between about 0° and about 55°, between about 0° and about 45°, between about 0° and about 35°, between about 0° and about 25°, between about 0° and about 15°, or between about 0° and about 5°.

In some implementations, the pullout resistor 104 and the retaining members 308 can extend from the elongated structure 112. The retaining members 308 can be integral to the elongated structure 112. For example, elongated structure 112 and the retaining members 308 can be formed at the same time from a mold that is injection molded to form the elongated structure 112 and retaining members 308. In some implementations, the pullout resistor 104 and the retaining members 308 can be coupled with the elongated structure 112. For example, the retaining members 308 can be glued to the external surface 300 of the elongated structure 112. In some implementations, when the retaining members 308 are coupled with the elongated structure 112, the retaining members 308 can become integral to the elongated structure 112. For example, the retaining members 308 and the elongated structure 112 can be bonded together with heat bonding.

The pullout resistor 104 can be manufactured with the same material or a different material than the elongated structure 112. For example, the pullout resistor 104 can include silicone, latex, polytetrafluoroethylene, polyethylene, polyurethane, polyvinyl chloride, polyether ether ketone, polysulfone, polypropylene, polycarbonate, or other polymer. In some implementations, the pullout resistor 104 can be manufactured from a denser or more rigid material when compared to the material of the elongated structure 112. In some implementations, the pullout resistor 104 can include metal or other materials. For example, each of the retaining members 308 can include a stainless steel backbone that provides rigid support to the retaining member 308.

As illustrated in FIG. 4, from the top view, the pullout resistor 104 is circular. In some implementations, the pullout resistor 104 can be any polygon shape. For example, the pullout resistor 104 can be triangular, square, pentagonal, hexagonal, etc. The pullout resistor 104 can include a plurality of slits 306. The slits 306 can extend from the perimeter of the pullout resistor 104 toward the elongated structure 112, which can define a lumen. In some implementations, the slits 306 can extend to a distance between about 0.5 mm and about 10 mm, between about 0.5 mm and about 8 mm, between about 0.5 mm and about 6 mm, or between about 0.5 mm and about 4 mm from the external surface 300 of the elongated structure 112. In some implementations, the slits 306 can extend to the outer diameter 300 of the elongated structure 112.

The slits 306 can run the length of the thickness 302 to form a plurality of retaining members 308. The pullout resistor 104 can include between about 2 and about 20, between about 2 and about 18, between about 2 and about 16, between about 2 and about 14, between about 2 and about 12, between about 2 and about 10, between about 2 and about 8, between about 2 and about 6, or between about 4 and about 6 retaining members 308. The thickness of each retaining member 308 can be between about 0.5 mm and about 5 mm, between about 0.5 mm and about 4.5 mm, between about 1 mm and about 4 mm, between about 1.5 mm and about 3.5 mm, or between about 2 mm and about 3 mm. Each of the retaining members 308 can extend from the external surface 300 of the elongated structure 112 to a length 304 between about 3 mm and about 15 mm, between about 5 mm and about 15 mm, or between about 5 mm and about 15 mm. The pullout resistor 104 can have a diameter or width between about 5 mm and about 30 mm, between about 10 mm and about 30 mm, between about 10 mm and about 25 mm, or between about 15 mm and about 25 mm. As illustrated in FIG. 3, the retaining members 308 can be of uniform thickness 302 along the length 304 of the retaining member 308. In some implementations, the thickness 302 of the retaining member 308 can taper along the length 304. For example, the retaining members 308 can be thinner toward the perimeter of the pullout resistor 104 or the retaining members 308 can be thinner toward the elongated structure 112.

Figures 5, 6:
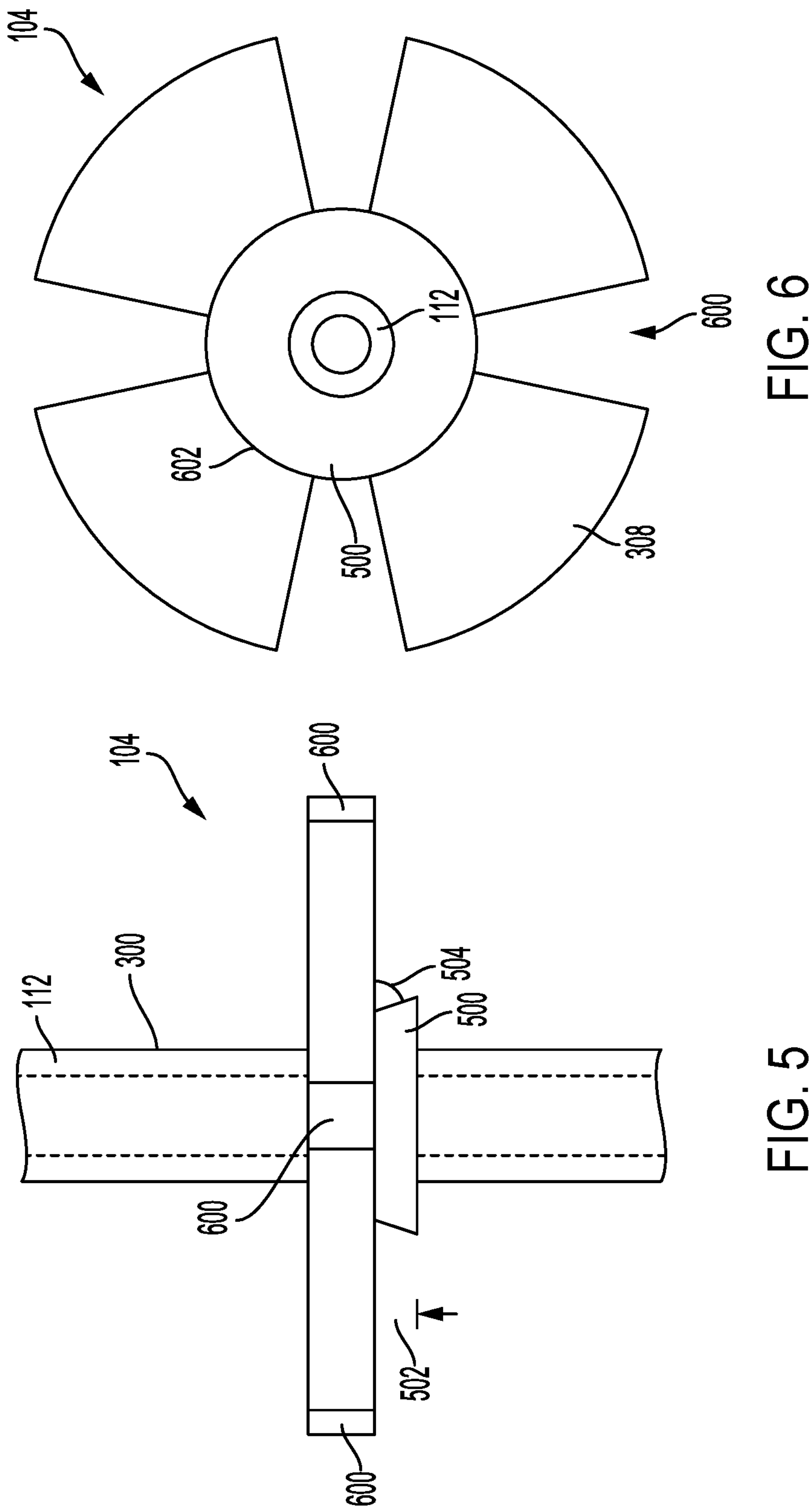
FIGS. 5 and 6 illustrate front and bottom views of an example pullout resistor that can be used with the example delivery device illustrated in FIG. 2.

FIGS. 5 and 6 illustrate front and bottom views, respectively, of a pullout resistor 104. Referring to FIGS. 5 and 6 together, pullout resistor 104 can include a plurality of retaining members 308. Each of the retaining members 308 can be separated by a spacing 600. In some implementations, the spacing 600 between each of the retaining members 308 can be equal. In some implementations, the spacing 600 can vary between the retaining members 308. In some implementations, each spacing 600 can occupy an arc of the pullout resistor's perimeter of between about 1° and about 135°, between about 1° and about 100°, between about 1° and about 80°, between about 5° and about 70°, between about 5° and about 60°, between about 10° and about 50°, between about 10° and about 40°, between about 10° and about 30°, or between about 10° and about 20°.

The pullout resistor 104 can include a lower retainer 500. The lower retainer 500 can include a beveled edge that forms an angle 504 with a face of the retaining members 308. The lower retainer 500 can control the deflection or collapse of the retaining members 308. For example, when a force is applied to a face of the retaining members 308 opposite the lower retainer 500, the maximum deflection angle of the retaining members 308 can be the angle 504. The joint between the retaining members 308 and the lower retainer 500 can form a fold line 602. The fold line 602 can be the location at which the retaining members 308 deflect or bend when a force is applied to the pullout resistor 104. In some implementations, as described further in relation to FIGS. 8 and 9, the fold line 602 can include a groove, cutout, perforation, hinge, or joint at which the retaining members 308 deflects towards the external surface 300. The lower retainer 500 can have a diameter between about 2 mm and about 15 mm, between about 5 mm and about 15 mm, or between about 10 mm and about 15 mm. The lower retainer 500 can have a thickness 502 of between about can be between about 0.5 mm and about 5 mm, between about 0.5 mm and about 4.5 mm, between about 1 mm and about 4 mm, between about 1.5 mm and about 3.5 mm, or between about 2 mm and about 3 mm.

Figure 7:
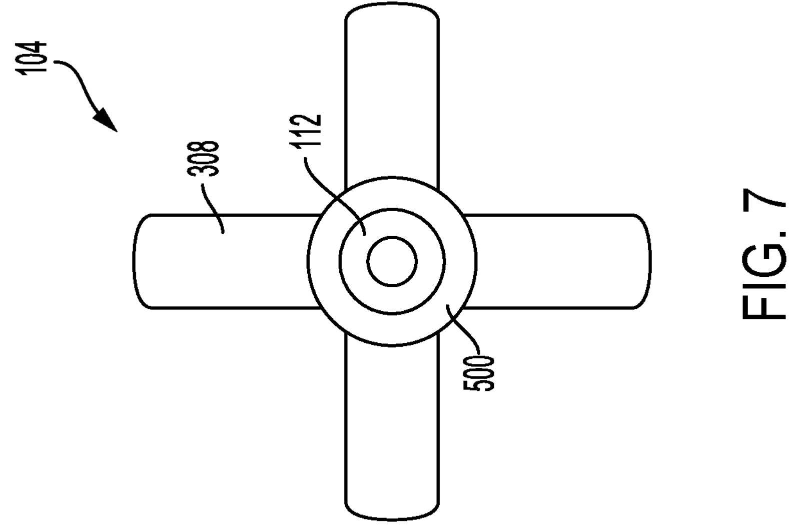
FIG. 7 illustrates a top-view of an example pullout resistor that can be used with the example delivery device illustrated in FIG. 2.

FIG. 7 illustrates a top-view of an example pullout resistor 104. FIG. 7 illustrates an example pullout resistor 104 where the retaining members 308 are configured in a leg configuration rather than a polygon configuration as illustrated in FIGS. 3-6. The retaining members 308 can be legs that extend from the external surface 300.

Figure 8:
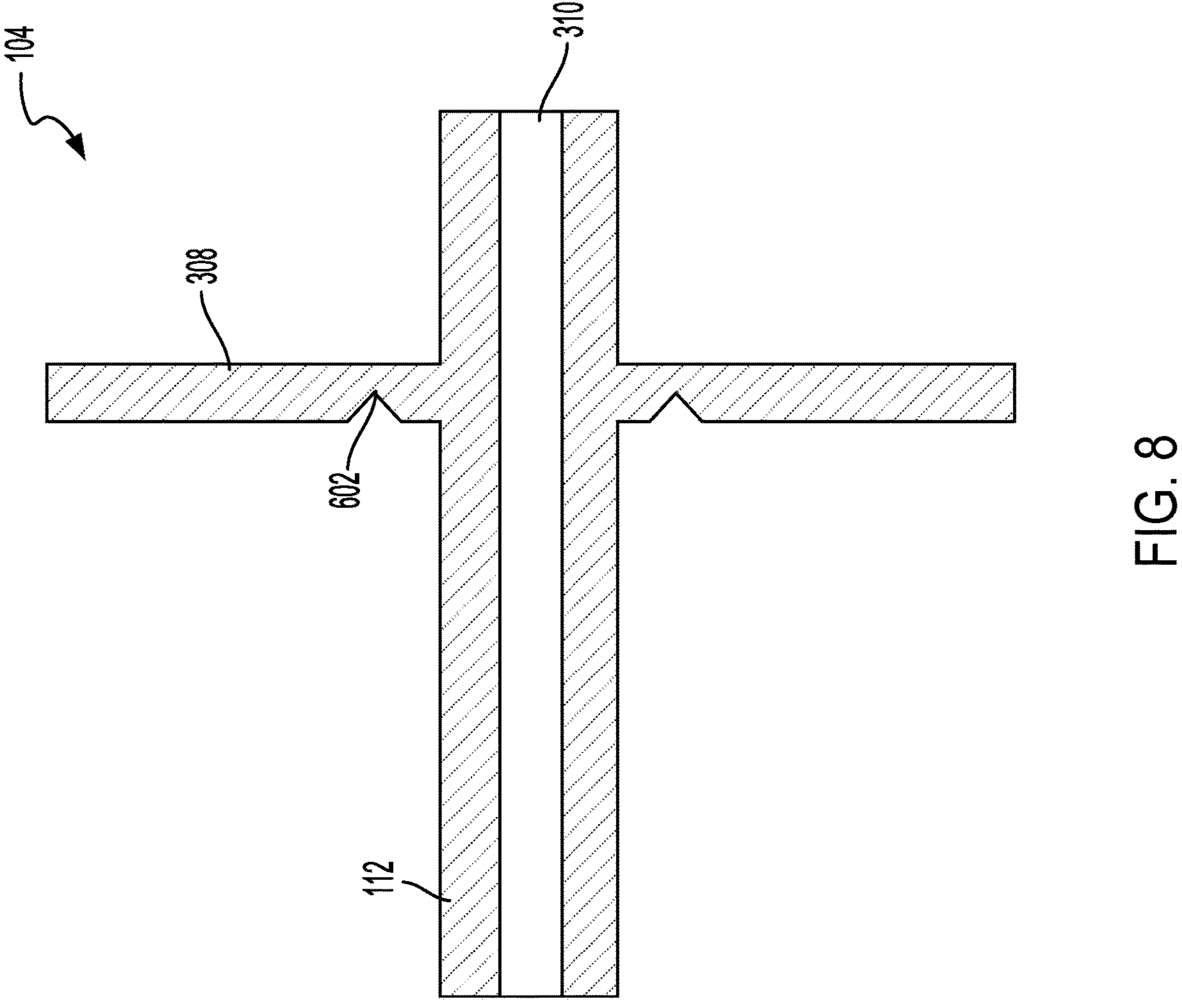
FIGS. 8 and 9 illustrate a cross-sectional view of an example pullout resistor in a deployed and collapsed state.
Figure 9:
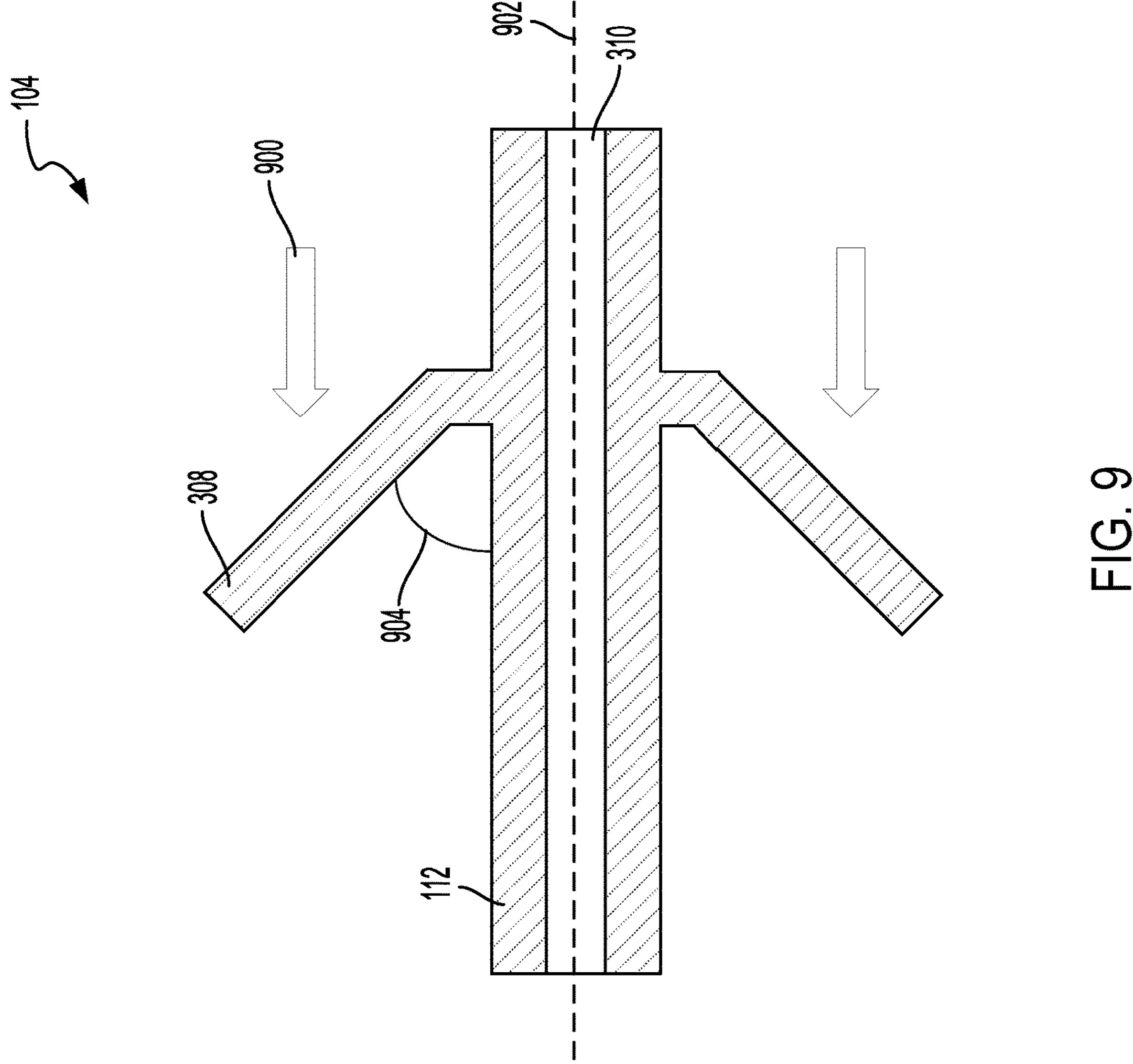

FIGS. 8 and 9 illustrate cross-sectional views of an example pullout resistor 104. The pullout resistor 104 can be similar to one of the above-described pullout resistors 104. For example, the pullout resistor 104 illustrated in FIGS. 8 and 9 can be similar to the pullout resistor 104 illustrated in FIGS. 5 and 6.

FIG. 8 illustrates the example pullout resistor 104 in the deployed state. In the deployed state, the retaining members 308 are substantially perpendicular to the elongated structure 112. The elongated structure 112 can define a lumen 310. The pullout resistor 104 can include a fold line 602 that passes through each of the retaining members 308. In some implementations, as illustrated in FIG. 8, the retaining member 308 can include a fold line 602 configured as a groove or channel formed in the retaining members 308. The fold line 602 can form a hinge. For example, the fold line 602 can form a living hinge between the retaining members 308 and the elongated structure 112 about which the retaining members 308 deflect.

FIG. 9 illustrates the pullout resistor 104 in the collapsed state. A force 900 can be applied in a direction along or parallel with the longitudinal axis 902. For example, the healthcare professional can grasp and pull on the elongated structure 112 external to the patient. The force 900 can be applied to the retaining members 308 by the abdominal wall 114 as the retaining members 308 come into contact with the abdominal wall 114. The retaining members 308 can collapse or deflect toward the elongated structure 112. The deflected retaining members 308 can form an angle between about 0° and about 55°, between about 0° and about 45°, between about 0° and about 35°, between about 0° and about 25°, between about 0° and about 15°, or between about 0° and about 5° with the external surface 300. The fold line 602 can control the angle 904. For example, when the fold line 602 is configured as a groove (as illustrated in FIG. 8), the greater the angle of the groove, the farther the walls of the groove can travel before coming into contact with one another and the further the retaining members 308 can deflect, which can result in a smaller angle 904.

When in the deployed state, the diameter of the pullout resistor 104 can prevent the delivery device 102 from being removed through the incision through which the elongated structure 112 passes in the abdominal wall 114. In the collapsed state, the diameter of the pullout resistor 104 is reduced as the retaining members 308 deflect toward the external surface 300. The reduced diameter of the pullout resistor 104 can enable the pullout resistor 104 to pass through the incision and the delivery device 102 to be removed from the patient.

Figure 10:
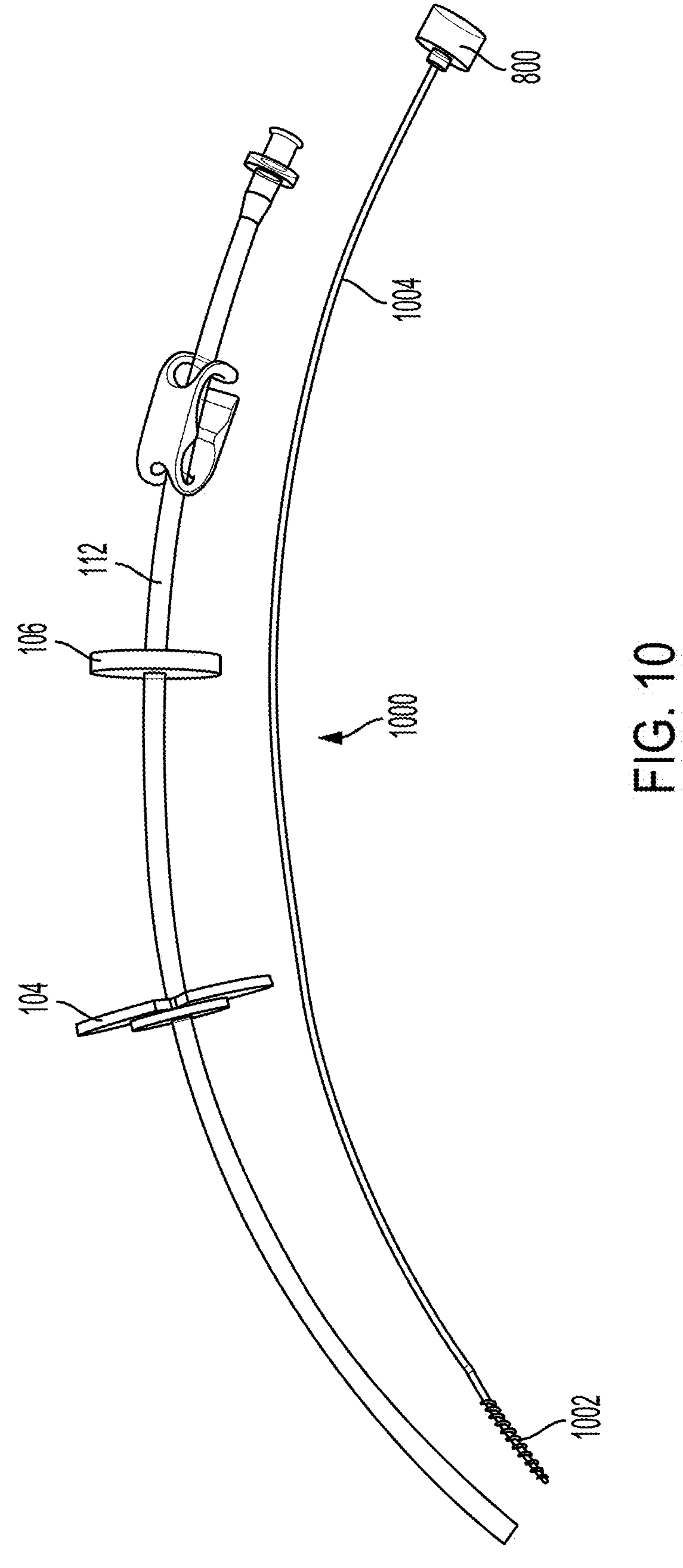
FIGS. 10 and 11 illustrate an example delivery device and brush.
Figure 11:
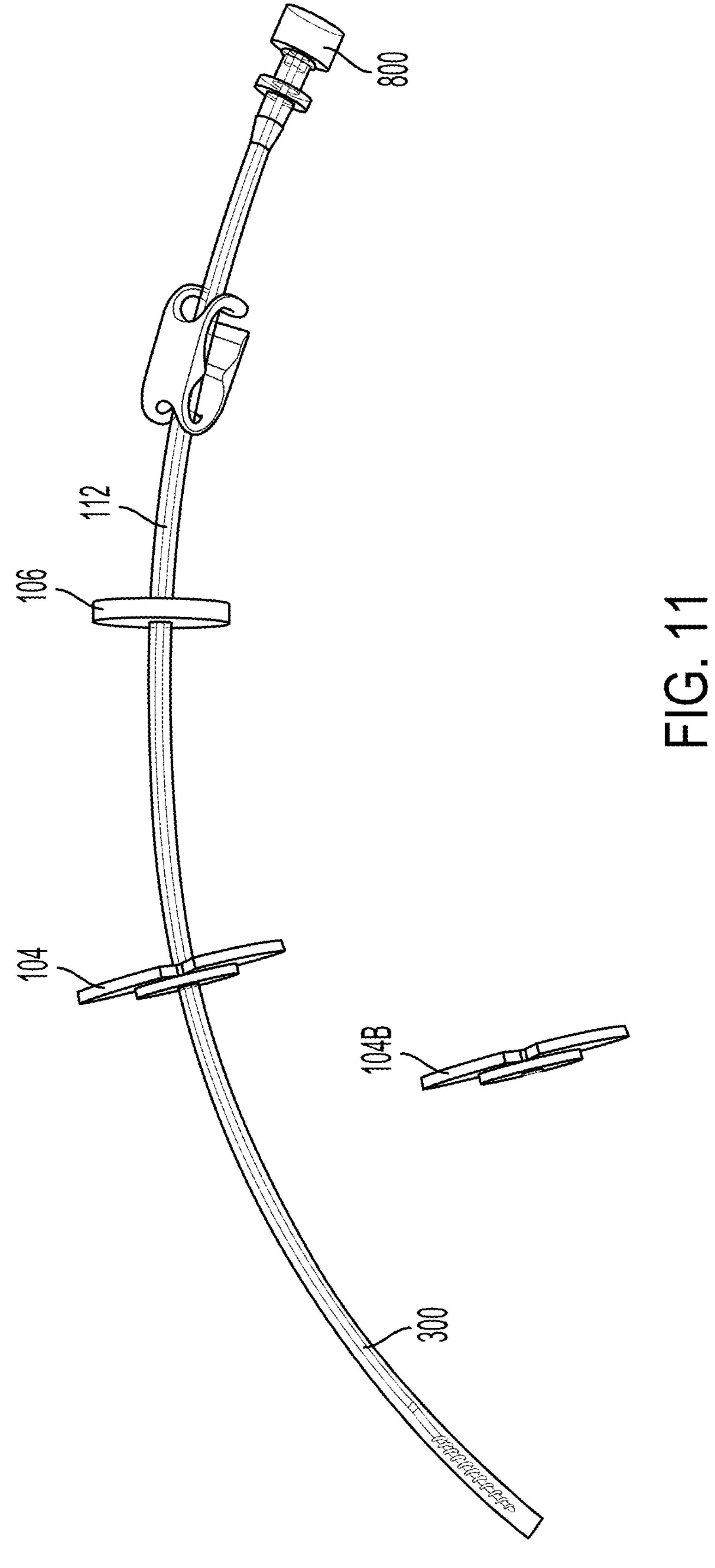

FIGS. 10 and 11 illustrate an example delivery device 102 and brush 1000. FIG. 10 illustrates the brush 1000 removed from the delivery device 102. FIG. 11 illustrates the brush 1000 disposed within the delivery device 102. The brush 1000 can be included in a kit with the delivery device 102. The kit can also include one or more washers 106, pullout resistors 104, and closure devices 200. In some implementations, the kit can include a syringe or funnel for injecting or flowing fluid into the delivery device 102. The kit can include two pullout resistors (first pullout 104 and second pullout resistor 104B as shown in FIG. 11) having two different material hardnesses (with different forces required to remove).

The brush 1000 can have a shaft 1004 with an outer diameter less than the inner diameter of the delivery device's lumen 310 such that the brush 1000 can be passed into the delivery device's lumen 310. A patient or healthcare professional can use the brush 1000 to clean the lumen 310 or to dislodge material from the lumen 310. The brush 1000 can include a plurality of bristles 1002 disposed toward a tip of the brush 1000. When passed through the lumen 310, the bristles 1002 can come into contact with walls of the lumen 310 to dislodge material from the walls or otherwise clean the lumen 310. The shaft 1004 can have a diameter between about 1 mm and about 5 mm between about 1 mm and about 4 mm, or between about 1 mm and about 3 mm. The shaft 1004 can include metal (e.g., stainless steel) or a plastic.

The brush 1000 can have a length equal to the length of the delivery device 102 such that when the brush 1000 is disposed within the lumen of the delivery device 102, the tip of the brush 1000 does not extend through the outlet and into the small intestine 116 of the patient. The brush 1000 can have a length less than the length of the delivery device 102. In some implementations, the brush 1000 can have a length greater than the length of the delivery device 102. For example, the brush 1000 can have a length that is between about 1 mm and about 5 cm, between about 1 mm and about 4 cm, between about 1 mm and about 3 cm, between about 1 mm and about 2 cm, or between about 1 mm and about 1 cm longer than a length of the delivery device 102.

Figure 12:
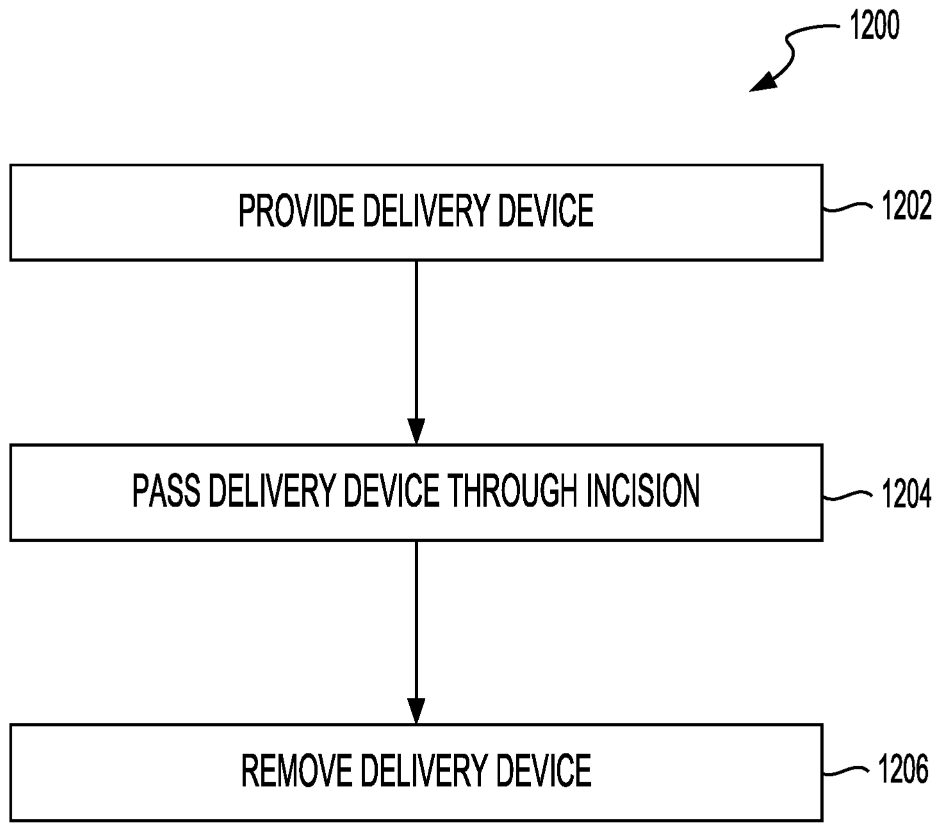
FIG. 12 illustrates a block diagram of an example method to implant the delivery device.

FIG. 12 illustrates a block diagram of an example method 1200 to use a delivery device. The method 1200 can include providing a delivery device (BLOCK 1202). The method 1200 can include passing the delivery device through an incision (BLOCK 1204). The method 1200 can include removing the delivery device (BLOCK 1206).

As set forth above, the method 1200 can include providing a delivery device (BLOCK 1202). Also, referring to FIGS. 1 and 2, among others, the delivery device 102 can include an elongated structure 112. The elongated structure 112 can be a tube that defines a lumen and includes a first and a second opening. The elongated structure 112 can be configured to delivery fluid through the lumen of the elongated structure 112. The delivery device 102 can include one or more pullout resistors 104. The pullout resistors 104 can extend from the elongated structure 112. The pullout resistor 104 can secure the delivery device 102 in place. For example, the pullout resistor 104 can anchor the delivery device 102 to an intraperitoneal face 118 of a patient's abdominal wall 114. The pullout resistor 104 can include a plurality of retaining members 308. The pullout resistor 104 can have a deployed state where the retaining members 308 are substantially perpendicular to the elongated structure 112. The pullout resistor 104 can have a collapsed or retracted state where the retaining members 308 are collapsed or deflected toward the elongated structure 112. In some implementations, the delivery device 102 can be provided as a component of a kit. The kit can include a delivery device 102 and a brush to clean the lumen of the delivery device 102. In some implementations, the kit can include an elongated structure 112, one or more pullout resistors 104, and one or more washers 106. For example, the elongated structure 112 can be a tube to which a surgeon can couple the pullout resistor 104 and the washer 106.

The method 1200 can include passing the delivery device through an incision (BLOCK 1204). The incision can be an incision in the abdominal wall of a patient. The method 1200 can also include passing the delivery device 102 through an incision in the patient's stomach or small intestine 116. The incisions in the patient can be made surgically or endoscopically. A portion of the elongated structure 112 can be passed through the incision in the abdominal wall 114 and into the target tissue. For example, the opening 110 can be implanted into the small intestine 116. In some implementations, the distal end of the elongated structure 112 that includes the opening 110 can be secured to the small intestine 116 with a Witzel Tunnel.

The pullout resistor 104 can be brought into contact with the intraperitoneal face 118 of the abdominal wall 114. In some implementations, the delivery device 102 can be secured to the abdominal wall 114 by clamping the abdominal wall 114 between the pullout resistor 104 and a washer 106 that is coupled with an external portion of the elongated structure 112. For example, a surgeon can slide the washer 106 along the longitudinal axis of the elongated structure 112 toward the external surface of the abdominal wall 114 (e.g., the skin surface of the patient's abdomen). The washer 106 can be held in place at the longitudinal position of the elongated structure 112 by a press fit. For example, the internal diameter of a hole through the washer 106 can be smaller than the outer diameter of the elongated structure 112. In some implementations, a clamp or a collar can be applied to the elongated structure 112 to secure the washer 106 in place.

In some implementations, the delivery device 102 can be implanted with the pullout resistor 104 in a retracted state and the pullout resistor 104 can be deployed once the delivery device 102 is passed through the incision and the pullout resistor 104 is within the intraperitoneal space. For example, the delivery device 102 can include a sheath that slides along the longitudinal axis of the elongated structure 112. During the implantation process, the sheath can be slid over the pullout resistor 104 to collapse the pullout resistor 104 toward the elongated structure 112. While in place, the sheath can restrain the pullout resistor 104 in the collapsed state. Once the pullout resistor 104 is in the intraperitoneal space, the sheath can be slid off the pullout resistor 104 to deploy the pullout resistor 104.

The method 1200 can include removing the delivery device (BLOCK 1206). In some implementations, the delivery device 102 can be chronically placed and is not removed from the patient. In other implementations, the delivery device 102 can be removed after a predetermined length of time. For example, the delivery device 102 can be implanted following a throat surgery that impedes the patient's ability to eat. Once the patient has healed and can resume orally consuming food, the delivery device 102 can be removed. The delivery device 102 can be removed by pulling the exposed portion of the elongated structure 112. A healthcare professional can apply a predetermined amount of force along the longitudinal axis of the elongated structure 112. The force can cause the retaining members 308 to collapse, which can reduce the diameter of the pullout resistor 104 and enable the pullout resistor 104 (and delivery device 102) to slide through the incision through the abdominal wall 114. In some implementations, the retaining members 308 can be retracted prior to applying the force along the longitudinal axis of the elongated structure 112. For example, the above described sheath can be slid over the retaining members 308 to collapse the retaining members 308 and then the delivery device 102 can be removed from the patient.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A kit comprising a feeding tube delivery device, the feeding tube delivery device comprising:

an elongated structure defining a lumen between a first opening at a first end and a second opening at a second end for delivery of a fluid to a small intestine of a subject in which the elongated structure is inserted; and a pullout resistor configured to anchor the elongated structure at an intraperitoneal face of an abdominal wall in a deployed state, the pullout resistor having a first pullout resistor material hardness, wherein the pullout resistor is configured to collapse or retract during implantation as the elongated structure is passed through an incision in the abdominal wall and to deploy after the pullout resistor is positioned within an intraperitoneal space between the abdominal wall and the small intestine of the subject, and wherein the pullout resistor is configured to collapse under a predetermined amount of force during passage of the pullout resistor through the incision during removal of the elongated structure from the subject, and wherein the predetermined amount of force is between 3 lbs and 20 lbs, and wherein the kit further comprises a second pullout resistor having a second pullout resistor material hardness, and wherein the first pullout resistor material hardness is different from the second pullout resistor material hardness such that the second pullout resistor is configured to collapse when a second predetermined amount of force, different from the predetermined amount of force, is applied in the direction along the longitudinal axis of the elongated structure.

2. The kit of claim 1, further comprising a washer configured to slide along a length of the longitudinal axis of the elongated structure to clamp the abdominal wall of the subject between the washer and the pullout resistor.

3. The kit of claim 1, wherein the pullout resistor comprises a plurality of retaining members projecting perpendicular to an external surface of the elongated structure.

4. The kit of claim 3, wherein the plurality of retaining members project perpendicular to the external surface of the elongated structure in the deployed state and deflect toward the external surface of the elongated structure in the collapsed state.

5. The kit of claim 1, wherein the pullout resistor comprises a plurality of retaining members and each of the plurality of retaining members has a thickness between 0.5 mm and 5 mm.

6. The kit of claim 1, wherein the pullout resistor comprises a plurality of retaining members and each of the plurality of retaining members has a length between 3 mm and 15 mm.

7. The kit of claim 1, wherein the pullout resistor has a pullout resistor material hardness configured for the predetermined amount of force being between 5 lbs and 10 lbs.

8. The kit of claim 1, wherein the elongated structure comprises a radiopaque strip extending along at least a portion of the elongated structure, an antibiotic or antimicrobial coating, and at least one of silicone, latex, polytetrafluoroethylene, polyethylene, polyurethane, and polyvinyl chloride.

9. The kit of claim 1, wherein the pullout resistor comprises a plurality of retaining members, and a thickness of the retaining members varies between an external surface of the elongated structure to an outer periphery of the pullout resistor.

10. The kit of claim 1, wherein the pullout resistor comprises a plurality of retaining members, and the retaining members are thinner toward an outer periphery of the pullout resistor than at inward portions of the pullout resistor.

11. The kit of claim 1, wherein the pullout resistor has a first retainer portion radially extending outwards from an external surface of the elongated structure to a second retaining portion that radially extends outwards from the first retainer portion to an outer periphery of the pullout resistor, and wherein the second retainer portion is thinner than the first retainer portion.

12. The kit of claim 1, wherein the pullout resistor is circular, wherein the pullout resistor has a first retainer portion radially extending outwards from an external surface of the elongated structure to a second retaining portion that radially extends outwards from the first retainer portion to an outer periphery of the pullout resistor, and wherein the first retainer portion forms an inner circle of the pullout resistor and the second retainer portion forms an outer circle of the pullout resistor.

13. The kit of claim 1, further comprising a sheath configured to slide over the pullout resistor to collapse the pullout resistor toward the elongated structure and thereby restrain the pullout resistor in the collapsed state during passage through the incision, wherein the sheath is configured to be removed from the pullout resistor to allow the pullout resistor to deploy within the intraperitoneal space thereby avoiding obstruction of a lumen of the small intestine.

14. The kit of claim 13, wherein the sheath is configured to be slid off the pullout resistor to deploy the pullout resistor.

15. A kit comprising:

a delivery device comprising:

an elongated structure comprising a first opening at a first end of the elongated structure and a second opening at a second end of the elongated structure, the elongated structure defining a lumen between the first opening and the second opening for delivery of a fluid to a subject in which the elongated structure is inserted;

a pullout resistor configured to anchor the elongated structure with an interior portion of an abdominal wall of the subject when the pullout resistor is in a deployed state and to collapse from the deployed state to a collapsed state when a predetermined amount of force is applied in a direction along a longitudinal axis of the elongated structure, wherein the pullout resistor is configured to be inserted into a body cavity in the collapsed state and to deploy from the collapsed state to the deployed state once the delivery device is passed through an incision and the pullout resistor is positioned within the body cavity;

a washer configured to slide along a length of the elongated structure to couple the abdominal wall between the washer and the pullout resistor; and a brush configured to slide within the lumen of the elongated structure;

wherein the pullout resistor has a first pullout resistor material hardness;

wherein the kit further comprises a second pullout resistor having a second pullout resistor material hardness; and wherein the first pullout resistor material hardness is different from the second pullout resistor material hardness such that the second pullout resistor is configured to collapse when a second predetermined amount of force, different from the predetermined amount of force, is applied in the direction along the longitudinal axis of the elongated structure.

16. The kit of claim 15, wherein the brush has a length less than a length of the delivery device.

17. The kit of claim 15, wherein the pullout resistor comprises a plurality of retaining members projecting perpendicular to an external surface of the elongated structure.

18. The kit of claim 17, wherein the plurality of retaining members project perpendicular to the external surface of the elongated structure in the deployed state and deflect toward the external surface of the elongated structure in the collapsed state.

19. The kit of claim 15, wherein the first pullout resistor material hardness is configured such that the predetermined amount of force is at least 8 lbs, and the second pullout resistor material hardness is configured such that the second predetermined amount of force is less than the predetermined amount of force.

* * * * *